US012423807B2

(12) United States Patent
Schwab

(10) Patent No.: US 12,423,807 B2
(45) Date of Patent: Sep. 23, 2025

(54) APPARATUS TO ANALYSE DIFFUSION MAGNETIC RESONANCE IMAGING DATA

(71) Applicant: KONINKLIJKE PHILIPS N.V., Eindhoven (NL)

(72) Inventor: Evan Schwab, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 543 days.

(21) Appl. No.: 17/796,687

(22) PCT Filed: Jan. 3, 2021

(86) PCT No.: PCT/EP2021/051894
§ 371 (c)(1),
(2) Date: Aug. 1, 2022

(87) PCT Pub. No.: WO2021/156122
PCT Pub. Date: Aug. 12, 2021

(65) Prior Publication Data
US 2023/0056838 A1    Feb. 23, 2023

Related U.S. Application Data

(60) Provisional application No. 62/969,188, filed on Feb. 3, 2020.

(51) Int. Cl.
*G06T 7/00*    (2017.01)
*A61B 5/00*    (2006.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC . G06T 7/0012; G06T 7/11; G06T 7/70; G06T 2207/10092; G06T 2207/20081;
(Continued)

(56) References Cited

U.S. PATENT DOCUMENTS 9,404,986 B2 *    8/2016    White ................. G01R 33/48
2010/0309223 A1 * 12/2010    Roth .......................... G06T 5/50
711/E12.001

(Continued)

OTHER PUBLICATIONS

Mueller Bryon A et al: 11Diffusion MRI and its Role in Neuropsychology,Neuropsychology Review, Plenum Press, New York, NY, US, vol. 25, No. 3, Aug. 9, 2015 (Aug. 9, 2015). pp. 250-271.

(Continued)

*Primary Examiner* — Matthew C Bella
*Assistant Examiner* — Andrew B. Jones

(57) ABSTRACT

An apparatus includes an input unit, a processing unit, and an output unit. The input unit is configured to provide the processing unit with at least one diffusion magnetic resonance imaging dMRI image of a patient's brain. The processing unit is configured to: 1) determine an estimate of an orientation of neurons at each voxel in the dMRI image; 2) determine a plurality of fiber tracts in the at least one dMRI image; 3) select a plurality of voxels along at least one fiber tract of the plurality of fiber tracts; and 4) determine a neurological disease classification.

10 Claims, 4 Drawing Sheets

(51) Int. Cl.
  *A61B 5/055*   (2006.01)
  *G01R 33/563*  (2006.01)
  *G06T 7/11*    (2017.01)
  *G06T 7/70*    (2017.01)

(52) U.S. Cl.
  CPC .......... *G01R 33/56341* (2013.01); *G06T 7/11* (2017.01); *G06T 7/70* (2017.01); *G06T 2207/10092* (2013.01); *G06T 2207/20081* (2013.01); *G06T 2207/20084* (2013.01); *G06T 2207/30016* (2013.01)

(58) Field of Classification Search
  CPC . G06T 2207/20084; G06T 2207/30016; A61B 5/0042; A61B 5/055; A61B 5/4088; G01R 33/56341; G01R 33/5608
  See application file for complete search history.

(56) References Cited

U.S. PATENT DOCUMENTS

| | | | | |
|---|---|---|---|---|
| 2011/0199084 | A1* | 8/2011 | Hasan | G01R 33/5608 324/309 |
| 2014/0294270 | A1* | 10/2014 | Schneider | A61B 5/055 382/131 |
| 2015/0279029 | A1 | 10/2015 | Jensen et al. | |
| 2016/0300352 | A1* | 10/2016 | Raj | G06V 10/764 |
| 2020/0297210 | A1* | 9/2020 | Gallacher | G01R 33/4806 |

OTHER PUBLICATIONS

Prasad Gautam et al: "Brain connectivity and novel network measures for Alzheimer's disease classification", Neurobiology of Aging, vol. 36, Aug. 30, 2014.

Jin Liling et al: "A ReliefF-SVM-based method for marking dopamine-based disease characteristics: A study on SWEDD and Parkinson's disease", Behavioural Brain Research, Elsevier, Amsterdam, NL, vol. 356, Sep. 9, 2018 (Sep. 9, 2018),pp. 400-407.

International Search Report and Written Opinion from PCT/EP2021/051894 mailed Apr. 20, 2021.

Graham, Benjamin, Martin Engelcke, and Laurens van der Maaten. "3d semantic segmentation with submanifold sparse convolutional networks." Proceedings of the IEEE Conference on Computer Vision and Pattern Recognition. 2018.

Graham, Benjamin "Spatially-sparse convolutional neural networks." arXiv preprint arXiv:1409.6070 (2014).

* cited by examiner

APPARATUS TO ANALYSE DIFFUSION MAGNETIC RESONANCE IMAGING DATA

CROSS REFERENCE TO RELATED APPLICATIONS

This application is a U.S. national phase application of International Application No. PCT/EP2021/051894 filed on Jan. 27, 2021, which claims the benefit of U.S. Application Ser. No. 62/969,188 filed on Feb. 3, 2020 and is incorporated herein by reference.

FIELD OF THE INVENTION

The present invention relates to an apparatus to analyse diffusion magnetic resonance imaging data, and imaging system and a method of analysing diffusion magnetic resonance imaging data.

BACKGROUND OF THE INVENTION

Diffusion MRI (dMRI) is a medical imaging modality used to reconstruct and visualize the anatomical network of neuronal fiber tracts in the brain, in vivo. This technology is important for analyzing anatomical brain connections, studying neurological and psychological disorders and discovering biomarkers for early detection of diseases such as Alzheimer's.

With feature maps (i.e. images formed by a scalar feature at every voxel), the standard procedure is to run voxel-wise statistical analyses over a population of spatially aligned healthy and diseased subjects to find statistically significant differences between feature values in certain regions of interest of the brain. Then, explanations can be formed about physical properties of diffusivity, which may be indicative of the disease based on the feature being studied. In terms of connectivity analysis, other common features are hand-crafted connectivity metrics from fiber tractography, such as the number, length, or density of fibers that connect different regions of interest. Additional features include averaging FA along the voxels occupied by the fiber tracts. This, however, does not incorporate small spatial variations along long fiber tracts over the brain. Once a connectivity matrix is created from these features, state of the art, invoke graph analysis to analyze the statistical properties of connectivity over populations of healthy and unhealthy subjects.

However, this technology is in its infancy, and further developments are required to provide effective disease classification.

SUMMARY OF THE INVENTION

It would be advantageous to have improved means of determining disease classification from diffusion magnetic resonance imaging data. The object of the present invention is solved with the subject matter of the independent claims, wherein further embodiments are incorporated in the dependent claims. It should be noted that the following described aspects and examples of the invention apply also to the apparatus to analyse diffusion magnetic resonance imaging data, and imaging system and the method of analysing diffusion magnetic resonance imaging data, as well as to the computer program element and a computer readable medium.

In a first aspect, there is provided an apparatus to analyse diffusion magnetic resonance imaging data, the apparatus comprising:

an input unit;
a processing unit; and
an output unit.

The input unit is configured to provide the processing unit with at least one diffusion magnetic resonance imaging "dMRI" image of a patient's brain. The processing unit is configured to determine an estimate of an orientation of neurons at each voxel in the dMRI image, the determination comprising utilization of the at least one dMRI image. The processing unit is configured to determine a plurality of fiber tracts in the at least one dMRI image, the determination comprising utilization of the estimated orientation of neurons at each voxel in the at least one dMRI image. The processing unit is configured to select a plurality of voxels along at least one fiber tract of the plurality of fiber tracts. The processing unit is configured to determine a neurological disease classification, the determination comprising utilization of at least one diffusivity feature associated with each of the selected plurality of voxels. The output unit is configured to output the neurological disease classification.

In other words, input brain imagery is processed from which specific voxels are selected along fiber tracts in the brain and the associated diffusivity features are processed to determine a neurological disease classification.

In an example, the processing unit is configured to determine a diffusivity profile at each voxel in the at least one dMRI image. The determination of the estimated orientation of neurons at each voxel in the at least one dMRI image can comprise utilization of the diffusivity profile at each voxel in the at least one dMRI image.

In an example, the processing unit is configured to determine a spherical probability distribution function at each voxel in the at least one dMRI image. The determination of the estimated orientation of neurons at each voxel in the at least one dMRI image can comprise utilization of the spherical probability distribution function at each voxel in the at least one dMRI image.

In an example, the spherical probability distribution function at each voxel in the at least one dMRI image relates to probabilities of diffusion in a given direction at each voxel in the at least one dMRI image.

In an example, the determination of the estimated orientation of neurons at each voxel in the at least one dMRI image comprises utilization of a peak in the spherical probability distribution function at each voxel in the at least one dMRI image.

In other words, given a 3D probability distribution function in each voxel, like an ODF or diffusion tensor, fiber tracts are then reconstructed in the whole brain by following the peaks of each distribution function in each voxel.

In an example, the processing unit is configured to determine the at least one fiber tract of the plurality of fiber tracts, the determination comprising a determination of one or more fiber tracts that connect a first segmented region of the brain to a second segmented region of the brain.

In an example, the processing unit is configured to determine the at least one fiber tract of the plurality of fiber tracts, the determination comprising a determination of two or more fiber tracts that connect a plurality of segmented regions of the brain one to the other.

In an example, the processing unit is configured to determine at least one connectivity weight for two connected segmented regions based on the number of fiber tracts that connect the two connected segmented regions.

Thus, only two segmented regions need to be connected, and the fibre tracts between those can be taken into account when determining the neurological disease classification, but more connected segments can be taken into consideration.

In an example, the processing unit is configured to determine at least one connectivity weight for two connected segmented regions based on at least one diffusivity feature associated with each of a plurality of voxels along fiber tracts that connect the two connected segmented regions.

In other words, it can be determined that two regions are connected if some threshold is met, for instance, at least one fiber tract starts and ends in those regions. Then the strength of a connection can be considered based on using features like the number of fibers that connect two regions or other features based on the diffusivity features, like the average FA, or features that are learned from the data when doing a disease classification task. The number of fiber tracts and diffusivity features can be determined automatically, but can be "hand-crafted" where these features are selected manually by a user or these can be learned from that data using for example a deep network.

Furthermore, the connectivity weights can be used to provide a degree of saliency, where for example where multiple segmented regions are connected by fiber tracts, the connectivity weights can be used to determine which pairs of regions were important. This can aid in the determination of the neurological disease.

Also, the connectivity weights can be used to map the weights back to the individual voxels underlying the fiber tracts and visualize a fiber tract heat-map which could be additionally visualized on the actual fiber tracts themselves in addition to on the voxels. By mapping the connectivity weights back to individual voxels of fiber tracts, it is enabled to provide information on where in the brain a disease pathology could manifest.

In an example, the processing unit is configured to implement at least one trained machine learning algorithm, and wherein determination of the neurological disease comprises processing of the at least one diffusivity feature associated with each of the selected plurality of voxels by the at least one trained machine learning algorithm.

In an example, the at least one trained machine learning algorithm is at least one 3D convolutional neural network (CNN).

In an example, the processing unit is configured to select voxels to be input to the at least one trained machine learning algorithm for active or non-zero voxels of the plurality of pixels along the at least one fiber tract.

In other words, one or more sparse 3D convolutional neural networks (CNN) can be utilized that applies (or apply) convolutional filters only around the sparse set of active, or nonzero, voxels occupying the fiber tract paths between brain regions. This not only speeds up computation because of the highly sparse number of active voxels in the entire brain volume, but also preserves the fiber tract shape unlike traditional convolutional filters.

In an example, the trained machine learning algorithm is trained on the basis of a plurality of dMRI images of reference patient's brains and information relating to neurological disease information for each of the reference patients.

In a second aspect, there is provided an imaging system, comprising:
a magnetic resonance image unit; and
an apparatus according to the first aspect.

The magnetic resonance imaging unit is configured to acquire at least one diffusion magnetic resonance imaging "dMRI" image of a patient's brain, and provide the at least one dMRI image to the apparatus. The apparatus is configured to output a neurological disease classification for the patient on the basis of the least one dMRI image.

In a third aspect, there is provided a method of analysing diffusion magnetic resonance imaging data, the method comprising:
a) providing a processing unit with at least one diffusion magnetic resonance imaging "dMRI" image of a patient's brain;
b) determining by the processing unit an estimate of an orientation of neurons at each voxel in the dMRI image, the determining comprising utilizing the at least one dMRI image;
c) determining by the processing unit a plurality of fiber tracts in the at least one dMRI image, the determining comprising utilizing the estimated orientation of neurons at each voxel in the at least one dMRI image;
d) selecting by the processing unit a plurality of voxels along at least one fiber tract of the plurality of fiber tracts;
e) determining by the processing unit a neurological disease classification, the determination comprising utilizing at least one diffusivity feature associated with each of the selected plurality of voxels; and
f) outputting by an output unit the neurological disease classification.

According to another aspect, there is provided a computer program element controlling one or more of the apparatuses or systems as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
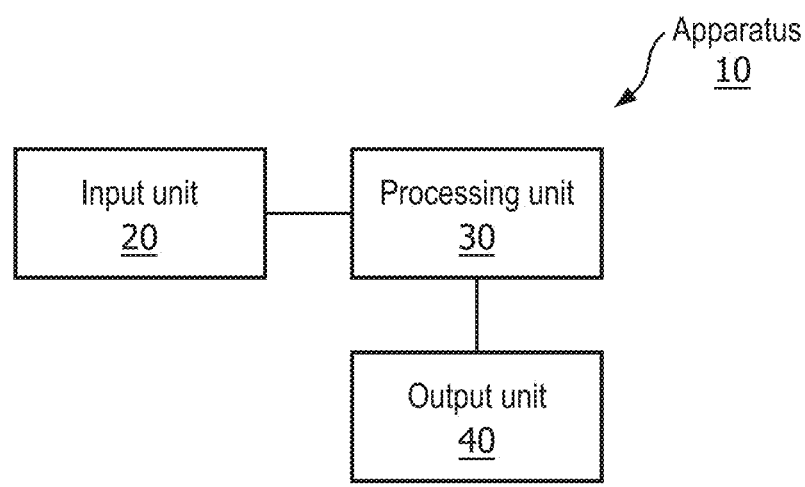
FIG. 1 shows a schematic set up of an example of an apparatus to analyse diffusion magnetic resonance imaging data.

FIG. 1 shows an example of an apparatus 10 to analyse diffusion magnetic resonance imaging data. The apparatus comprises an input unit 20, a processing unit 30, and an output unit 40. The input unit is configured to provide the processing unit with at least one diffusion magnetic resonance imaging "dMRI" image of a patient's brain. The processing unit is configured to determine an estimate of an orientation of neurons at each voxel in the dMRI image, the determination comprising utilization of the at least one dMRI image. The processing unit is configured to determine a plurality of fiber tracts in the at least one dMRI image, the determination comprising utilization of the estimated orientation of neurons at each voxel in the at least one dMRI image. The processing unit is configured to select a plurality of voxels along at least one fiber tract of the plurality of fiber tracts. The processing unit is configured to determine a neurological disease classification, the determination comprising utilization of at least one diffusivity feature associated with each of the selected plurality of voxels. The output unit is configured to output the neurological disease classification.

It is to be noted that the dMRI image can be acquired in a number of different gradient schemes and then estimation of the diffusivity profiles can be calculated in a number of ways including the diffusion tensor, which all together can here be termed "Diffusion Tensor Imaging". Other types of protocols include High Angular Resolution Diffusion Imaging (HARDI), which estimates an orientation distribution function (ODF), i.e. spherical probability distribution function, at every voxel instead of a diffusion tensor.

However, the apparatus, system and method described here cover any and all imaging protocols that then estimate any and all diffusivity profiles that are used for tractography.

According to an example, the processing unit is configured to determine a diffusivity profile at each voxel in the at least one dMRI image. The determination of the estimated orientation of neurons at each voxel in the at least one dMRI image can comprise utilization of the diffusivity profile at each voxel in the at least one dMRI image.

According to an example, the processing unit is configured to determine a spherical probability distribution function at each voxel in the at least one dMRI image. The determination of the estimated orientation of neurons at each voxel in the at least one dMRI image can comprise utilization of the spherical probability distribution function at each voxel in the at least one dMRI image.

According to an example, the spherical probability distribution function at each voxel in the at least one dMRI image relates to probabilities of diffusion in a given direction at each voxel in the at least one dMRI image.

According to an example, the determination of the estimated orientation of neurons at each voxel in the at least one dMRI image comprises utilization of a peak in the spherical probability distribution function at each voxel in the at least one dMRI image.

According to an example, the processing unit is configured to determine the at least one fiber tract of the plurality of fiber tracts, the determination comprising a determination of one or more fiber tracts that connect a first segmented region of the brain to a second segmented region of the brain.

In an example, the first segmented region of the brain and the second segmented region of the brain are determined from a brain atlas.

In other words, brain regions are segmented into possibly 100s of regions based on the anatomy of the brain given by an atlas. Given these brain region segmentations, it is then determined which regions are physically connected by fiber tracts that start and end in a pair of regions. Not all regions are connected, or joined to all other regions and the regions that are connected can be identified and the most important regions or indeed pair of regions and the fiber tracts connecting them selected for processing for disease classification.

According to an example, the processing unit is configured to determine the at least one fiber tract of the plurality of fiber tracts, the determination comprising a determination of two or more fiber tracts that connect a plurality of segmented regions of the brain one to the other.

According to an example, the processing unit is configured to determine at least one connectivity weight for two connected segmented regions based on the number of fiber tracts that connect the two connected segmented regions.

According to an example, the processing unit is configured to determine at least one connectivity weight for two connected segmented regions based on at least one diffusivity feature associated with each of a plurality of voxels along fiber tracts that connect the two connected segmented regions.

According to an example, the processing unit is configured to implement at least one trained machine learning algorithm. The determination of the neurological disease can comprise processing of the at least one diffusivity feature associated with each of the selected plurality of voxels by the at least one trained machine learning algorithm.

According to an example, the at least one trained machine learning algorithm is at least one 3D convolutional neural network (CNN).

According to an example, the processing unit is configured to select voxels to be input to the at least one trained machine learning algorithm for active or non-zero voxels of the plurality of pixels along the at least one fiber tract.

For more information on sparse CNNs see for example: Graham, Benjamin, Martin Engelcke, and Laurens van der Maaten. "3d semantic segmentation with submanifold sparse convolutional networks." Proceedings of the IEEE Conference on Computer Vision and Pattern Recognition. 2018, and Graham, Benjamin. "Spatially-sparse convolutional neural networks." arXiv preprint arXiv:1409.6070 (2014).

In an example, the at least one 3D convolutional neural network comprises at least one sparse 3D convolutional network.

In an example, when there are three or more segmented regions of the brain the processing unit is configured to implement a sparse 3D convolutional network for each pair of segmented regions. Thus, a sparse 3D convolutional network is implemented for the fiber tracts that connect each pair of regions under consideration. In other words, the processing of structural connectivity maps between brain regions for classification of neurological diseases comprises combing sparse 3D CNNs for each set of fiber tract connections between those brain regions.

In an example, the processing unit is configured to apply a sparse 3D CNN to each pair of segmented brain regions to determine a feature vector for that pair of segmented brain regions and concatenate the feature vectors for pairs of brain regions in a last fully connected layer, the output of which is the classification of neurological disease.

According to an example, the trained machine learning algorithm is trained on the basis of a plurality of dMRI images of reference patient's brains and information relating to neurological disease information for each of the reference patients.

Thus, a novel way is provided to process structural connectivity maps between brain regions identified in a brain atlas within a deep learning framework for the classification of neurological diseases. A sparse convolutional neural network (CNN) is applied to dMRI features extracted from 3D voxels along fiber tracts that structurally connect brain regions of interest. In this way, an end-to-end deep learning pipeline is provided which takes dMRI diffusivity features, such as the fractional anisotropy (FA), as input for each set of fiber connections and outputs a disease classification. In addition, because each fiber connection is taken as multiple inputs to the network, gradient based saliency mapping can be used to visualize the contribution of each fiber connection to the end classification.

There are two degrees of saliency that can be considered. The first is to consider the weights of each pair of segmented regions to see which were important. The second is to use saliency to map the weights back to the individual voxels underlying the fiber tracts and visualize a fiber tract heatmap, which could be additionally visualized on the actual fiber tracts themselves in addition to on the voxels. The first can used within a connectivity matrix framework already. The second can be applied when it is desired to know where in the brain a disease pathology might manifest.

In other words, a deep learning pipeline for disease classification of dMRI data is provided. The inputs to this are 1) diffusivity features per voxel such as FA from for example diffusion tensor estimation, 2) fiber tracts reconstructed from for example diffusion tensor peaks through fiber tractography, 3) segmented brain regions from a brain atlas, and 4) structural connectivity based on physical fiber tracts connecting pairs of brain regions. From these inputs, voxels are extracted along which fiber tracts connect each pair of brain regions. The features of these voxels for each pair of brain regions is an input to this multi-input deep neural network. A (non-traditional) sparse 3D CNN is then applied to these 3D feature volumes and a feature vector for each brain region pair is output and the results are concatenated in a last fully connected layer. The output to this multi-input network is a classification of neurological disease based on training data classes.

Figure 2:
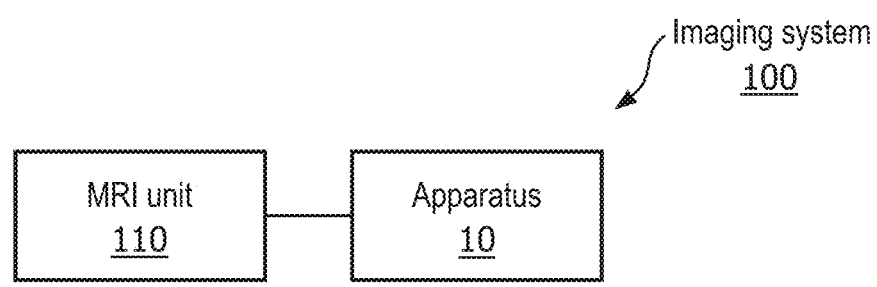
FIG. 2 shows a schematic set up of an example of an imaging system.

FIG. 2 shows an example of an imaging system 100. The imaging system comprises a magnetic resonance image unit 110, and an apparatus 10 as described with reference to FIG. 1. The magnetic resonance imaging unit is configured to acquire at least one diffusion magnetic resonance imaging "dMRI" image of a patient's brain, and provide the at least one dMRI image to the apparatus. The apparatus is configured to output a neurological disease classification for the patient on the basis of the least one dMRI image.

Figure 3:
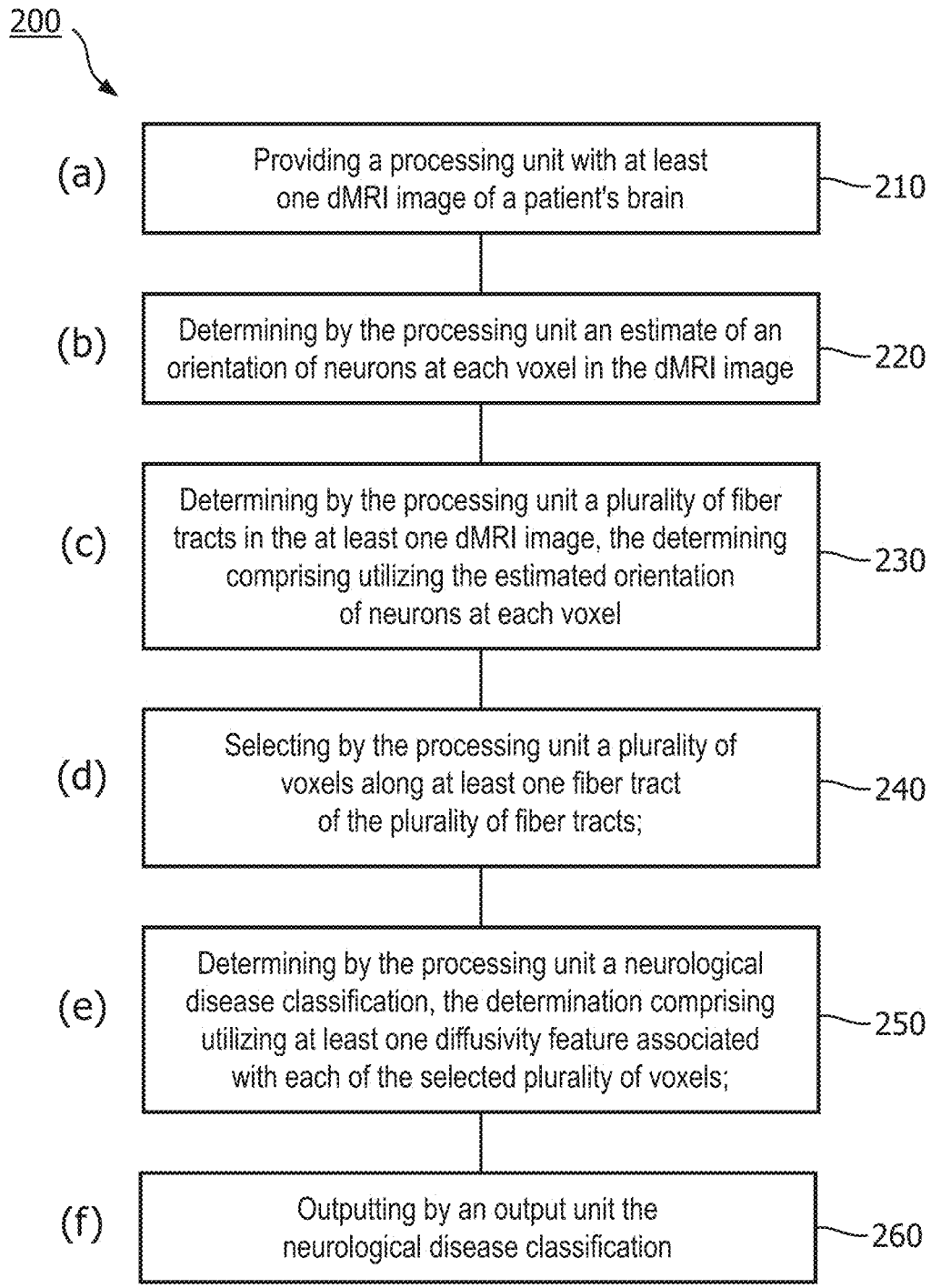
FIG. 3 shows a method of analysing diffusion magnetic resonance imaging data.

FIG. 3 shows a method 200 of analysing diffusion magnetic resonance imaging data in its basic steps. The method comprises:

in a providing step 210, also referred to as step a), providing a processing unit with at least one diffusion magnetic resonance imaging "dMRI" image of a patient's brain;

in a determining step 220, also referred to as step b), determining by the processing unit an estimate of an orientation of neurons at each voxel in the dMRI image, the determining comprising utilizing the at least one dMRI image;

in a determining step 230, also referred to as step c), determining by the processing unit a plurality of fiber tracts in the at least one dMRI image, the determining comprising utilizing the estimated orientation of neurons at each voxel in the at least one dMRI image;

in a selecting step 240, also referred to as step d), selecting by the processing unit a plurality of voxels along at least one fiber tract of the plurality of fiber tracts;

in a determining step 250, also referred to as step e), determining by the processing unit a neurological disease classification, the determination comprising utilizing at least one diffusivity feature associated with each of the selected plurality of voxels; and in an outputting step 260, also referred to as step f), outputting by an output unit the neurological disease classification.

In an example, the method comprises determining by the processing unit a diffusivity profile at each voxel in the at least one dMRI image, and wherein step b) comprises utilizing the diffusivity profile at each voxel in the at least one dMRI image.

In an example, the method comprises determining by the processing unit a spherical probability distribution function at each voxel in the at least one dMRI image, and wherein step b) comprises utilizing the spherical probability distribution function at each voxel in the at least one dMRI image.

In an example, the spherical probability distribution function at each voxel in the at least one dMRI image relates to probabilities of diffusion in a given direction at each voxel in the at least one dMRI image.

In an example, step b) comprises utilizing a peak in the spherical probability distribution function at each voxel in the at least one dMRI image.

In an example, step c) comprises determining the at least one fiber tract of the plurality of fiber tracts comprising determining one or more fiber tracts that connect a first segmented region of the brain to a second segmented region of the brain.

In an example, the first segmented region of the brain and the second segmented region of the brain are determined from a brain atlas.

In an example, step c) comprises determining the at least one fiber tract of the plurality of fiber tracts comprising determining two or more fiber tracts that connect a plurality of segmented regions of the brain one to the other In an example, the method comprises determining a connectivity weight for two connected segmented regions based on the number of fiber tracts that connect the two connected segmented regions.

In an example, the method comprises determining a connectivity weight for two connected segmented regions based on at least one diffusivity feature associated with each of a plurality of voxels along fiber tracts that connect the two connected segmented regions.

In an example, the method comprises implementing by the processing unit at least one trained machine learning algorithm, and wherein step e) comprises processing the at least one diffusivity feature associated with each of the selected plurality of voxels by the at least one trained machine learning algorithm.

In an example, the at least one trained machine learning algorithm comprises at least one 3D convolutional neural network.

In an example, the method comprises selecting by the processing unit voxels to be input to the at least one trained machine learning algorithm for active or non-zero voxels of the plurality of pixels along the at least one fiber tract.

In an example, the at least one 3D convolutional neural network comprises at least one sparse 3D convolutional network.

In an example, when there are three or more segmented regions of the brain the method comprises implementing by the processing unit a sparse 3D convolutional network for each pair of segmented regions.

In an example, the method comprises applying by the processing unit a sparse 3D CNN to each pair of segmented brain regions to determine a feature vector for that pair of segmented brain regions and concatenate the feature vectors for pairs of brain regions in a last fully connected layer, the output of which is the classification of neurological disease.

In an example, the trained machine learning algorithm is trained on the basis of a plurality of dMRI images of reference patient's brains and information relating to neurological disease information for each of the reference patients.

Figure 4:
FIG. 4 shows the structural connectivity of fiber tracts between regions of interest from a brain atlas.
Figure 5:
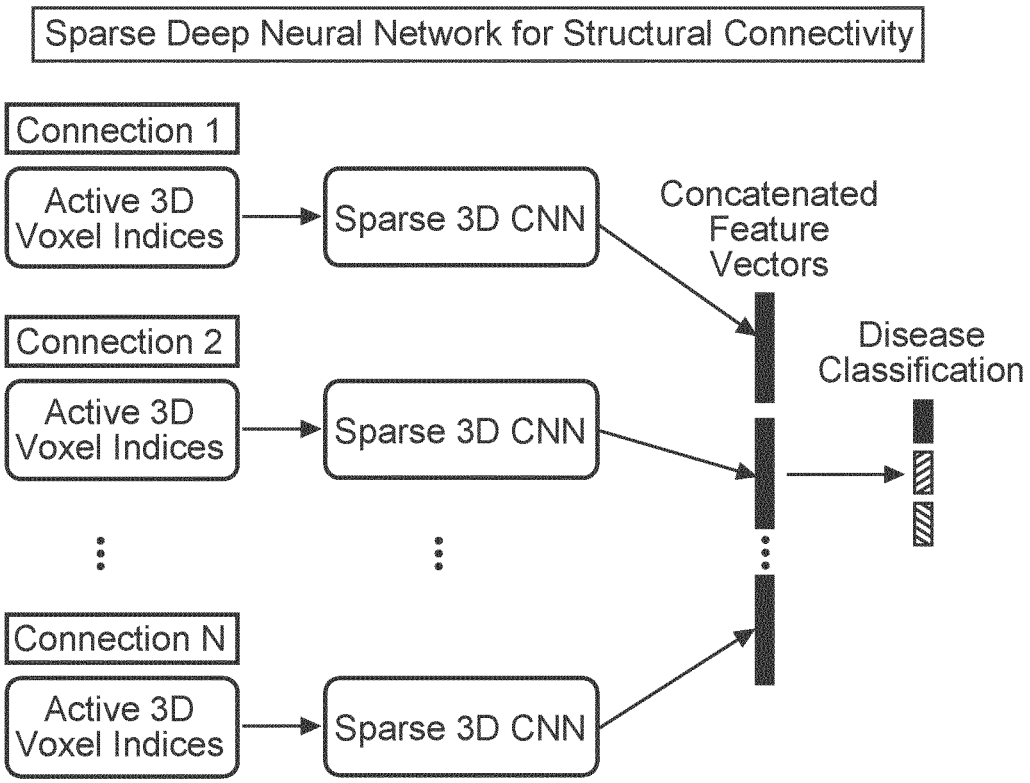
FIGS. 5-6 show Schematic representations of the Sparse Deep Neural Network for Structural Connectivity Based Disease Classification.
Figure 6:
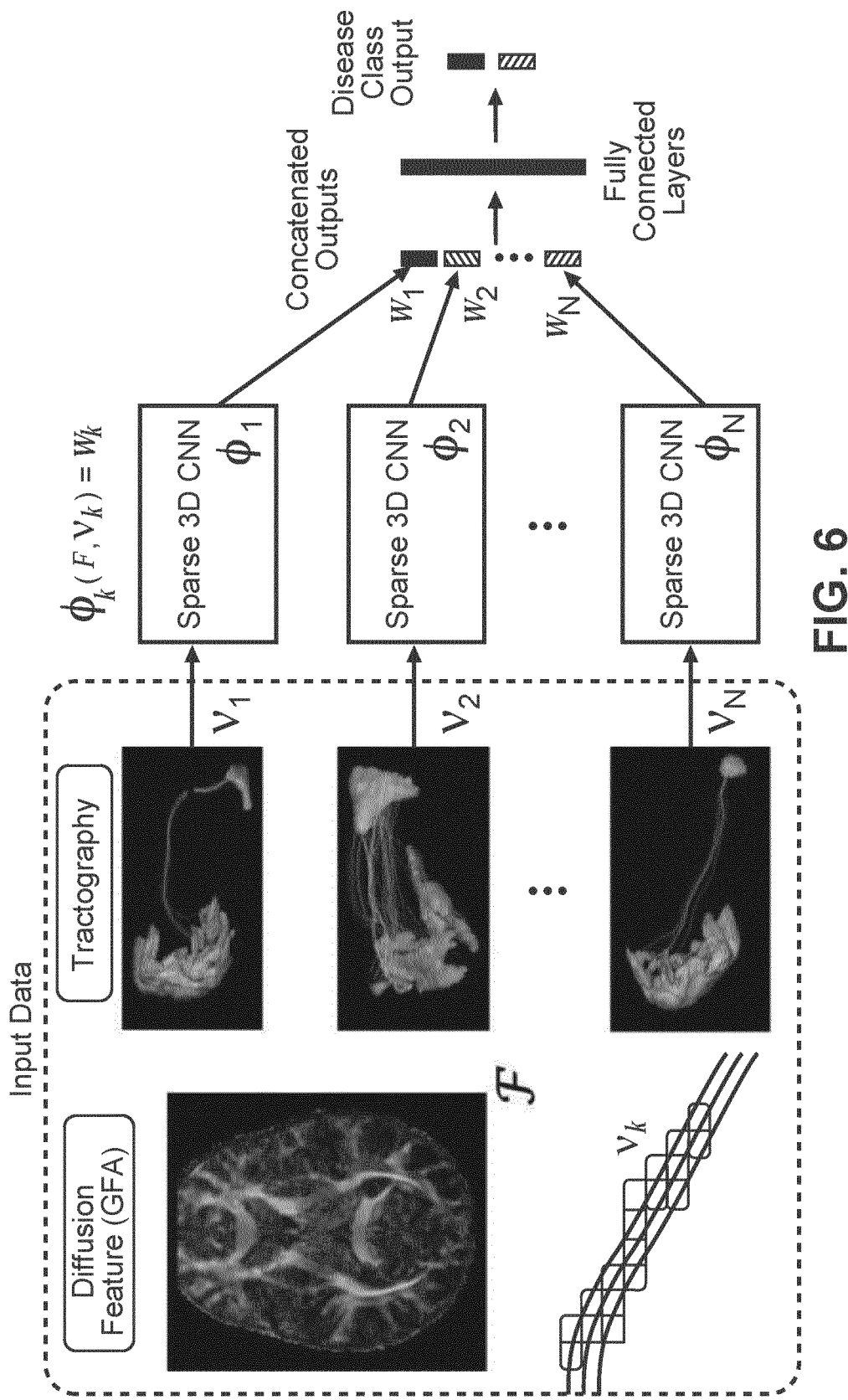

The apparatus to analyse diffusion magnetic resonance imaging data, imaging system and method of analysing diffusion magnetic resonance imaging data are now described in specific further detail, where reference is made to FIGS. 4-6.

Diffusion MM measures directional quantities of water diffusion in the brain by acquiring a set of diffusion weighted images to estimate the orientation of bundles of neurons at each voxel of a brain volume. These orientation estimations are modelled by spherical probability distribution functions such as a 3D Gaussian distribution known as a diffusion tensor in diffusion tensor imaging (DTI) or a non-parametric orientation distribution function (ODF) in high angular resolution diffusion imaging. Fiber tracts are then reconstructed by following the peaks of these spherical PDFs in each voxel.

DTI feature maps can be extracted from the eigenvalues of the diffusion tensors: fractional anisotropy (FA), mean diffusivity, axial diffusivity, radial diffusivity. The dMRI analysis described here relates to the analysis of such features, that are analytically computed from a pre-defined diffusion model, such as fractional anisotropy (FA) and mean diffusivity (MD) calculated from the eigenvalues of a diffusion tensor.

FIG. 4 shows Structural Connectivity of fiber tracts between regions of interest from a brain atlas. In classifying neurological disease as described here, in terms of connectivity analysis, connectivity metrics from fiber tractography are utilized, such as the number, length, or density of fibers that connect different regions of interest. Additional features include averaging FA, or other diffusivity measures, along the voxels occupied by the fiber tracts.

FIGS. 5-6 show schematics of the Sparse Deep Neural Network for Structural Connectivity Based Disease Classification developed and utilized here.

The main elements involve a deep learning pipeline for disease classification of dMRI data. The inputs to this invention are 1) diffusivity features per voxel such as FA from diffusion tensor estimation, 2) fiber tracts reconstructed from diffusion tensor peaks through fiber tractography, 3) segmented brain regions from a brain atlas, and 4) structural connectivity based on physical fiber tracts connecting pairs of brain regions (See FIG. 6). From these inputs, the voxels along which fiber tracts connect each pair of brain regions are extracted. The features of these voxels for each pair of brain regions is an input to this multi-input deep neural network. A CNN is applied to these 3D feature volumes and outputs a feature vector for each brain region pair, with this result output concatenated in a last fully connected layer.

However, rather than using a traditional 3D CNN, which would be computationally demanding because of the large size of the dMRI volume and the number of volume inputs for each pair of brain regions and would artificially diffuse the sparse feature signals along the thin fiber tract paths. Here a sparse 3D CNN is used, which applies convolutional filters only around the sparse set of active, or nonzero, voxels occupying the fiber tract paths between brain regions. This not only speeds up computation because of the highly sparse number of active voxels in the entire brain volume, but also preserves the fiber tract shape unlike traditional convolutional filters. The output to this multi-input network is a classification of neurological disease based on the training data classes.

In addition, saliency methods for deep neural networks can be invoked, which can identify the weights in the network that were responsible or the classification of a new subject. Because the network is divided between inputs for each brain connection, the saliency method can be used to track which brain connections were important for the classification and visualize with a heat-map along the input voxels and fiber tracts.

Thus, a workflow of the new neurological disease classification can be summarised as:
1. Obtain a diffusion MRI of the brain of a patient
2. Determine diffusivity features per voxel—features such as fractional anisotropy (FA), mean diffusivity, axial diffusivity, radial diffusivity determined from diffusion tensor estimation
3. Reconstruct fiber tracts from diffusion tensor peaks
4. Segment brain regions from a brain atlas
5. The fiber tracts at 3 are then used to join the segmented brain regions at 4
6. Use the fiber tracts at 5 to select voxels along the tracts
7. The diffusivity features at 2 for the voxels selected at 6 are then input into a sparse 3D CNN
8. A classification of neurological disease is output
9. Perform saliency mapping The Sparse CNN Network and Its Training Diffusion Feature(s) (like FA) and active voxel indices for each set of fiber tracts connecting region of interest pairs are used as input. A sparse 3D CNN is used for each pair of regions and either a vector or scalar is output and concatenated to form a large vector for the subject. The CNN architecture can for example be a sparse version of common CNN architectures like ResNet, VGG, Densenet. Then a series of fully connected layers, non-linear layers like ReLU, output to a disease prediction (e.g. binary, multi-class, regression) that is compared to the ground truth in a usual loss function like cross entropy and a usual gradient descent backpropagation algorithm is used to update all weights in the fully connected layers and each sparse 3D CNN. Thus, relating to disease prediction or classification any of the above machine learning tasks such as binary classification, multi-class classification, or regression can be used to output a continuous number, like in the case of severity prediction or cognitive scores.

The following two options can be used to relate the sparse CNNs. Each one could be trained independently (which would involve N times more weights), or one sparse CNN could be trained for which the weights are shared between all of the ROI pairs (this latter relates to a smaller network to train).

Saliency Mapping

This is in effect an add-on to the disease classification workflow described above. Regarding its implementation, there are saliency methods such as Gradient class activation mapping (GradCam) that can be utilized. This analyzes the weights of the network (after training, at test time) using back propagation, to find large weights which may correlate to the importance of giving the class prediction. First, it can be seen which of the fiber tracts were important for the class prediction based on the weights learned for each fiber tract as output by each sparse CNN. In addition, using the sparse CNN this can be used to visualize a heat-map of weights along the voxels selected in step 6 (discussed above) to see not only which fiber tracts were important but also which voxels along the fiber tracts were important.

Summary

Neurological disease classification is enabled by connecting neural network components in an end-to-end model. Voxel locations for fiber tracts that connect N region pairs are determined. Each of these is input to a sparse 3D CNN, which outputs a feature vector of reduced input size. These feature vectors are then concatenated to form a single feature vector than is fed into a set of fully connected layers that and finally outputs a class prediction for binary or multi-class classification or regression.

Then a saliency mapping can be applied on a new test subject after classification has been performed in order to visualize the important weights of the network as heat-maps along the voxel regions connecting each region of interest.

In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus to analyze diffusion magnetic resonance imaging data, the apparatus comprising:
   an input unit;
   a processing unit; and
   an output unit;
   wherein, the input unit is configured to provide the processing unit with set of diffusion-weighted diffusion magnetic resonance imaging (dMRI) images of a patient's brain;
   wherein, the processing unit is configured to determine an estimate of an orientation of neurons at each voxel of a brain volume in the dMRI image set, the determination comprising:
   determining a spherical probability distribution function at each voxel of the brain volume relating to probabilities of diffusion in a given direction at each voxel based on the set of dMRI images, and
   determining the estimated orientation of neurons at each voxel by utilizing a peak in the spherical probability distribution function at each voxel;
   wherein three or more regions of the brain volume in the set of dMRI images are segmented;
   wherein the processing unit is configured to determine at least one diffusivity feature for each voxel of the brain volume based on the set of dMRI images;
   wherein, the processing unit is configured to determine a plurality of fiber tracts in the brain volume in the dMRI image set using the estimated orientation of neurons at each voxel of the brain volume;
   wherein the processing unit is configured to identify a plurality of pairs of the segmented regions which are connected by fiber tracts to one another, and for each pair of connected segmented regions:
   select a plurality of voxels along fiber tracts connecting the pair of regions,
   provide the at least one diffusivity feature of each of the selected voxels as inputs to a multi-input deep neural network which comprises a respective sparse 3D convolutional neural network for each pair of segmented regions, wherein each respective sparse neural network outputs a respective feature vector for the pair of regions based on the input features, wherein, the processing unit is configured to determine a neurological disease classification, wherein the multi-input deep neural network concatenates the feature vectors generated for each of the pairs of brain regions in a further fully connected layer, and wherein an output of the multi-input deep neural network is the classification of the neurological disease; and wherein, the output unit is configured to output the neurological disease classification, wherein the multi-input deep neural network is trained on a basis of a plurality of dMRI image sets of reference patients' brains and information relating to neurological disease information for each of the reference patients.

2. The apparatus of claim 1, wherein the processing unit is configured to determine at least one connectivity weight for each connected pair of segmented regions based on the number of fiber tracts that connect the two connected segmented regions.

3. The apparatus of claim 1, wherein the processing unit is configured to determine at least one connectivity weight for each pair of connected segmented regions based on at least one diffusivity feature associated with each of a plurality of voxels along fiber tracts that connect the two connected segmented regions.

4. The apparatus of claim 1, wherein the processing unit is configured to select voxels to be input to the multi-input deep neural network for active or non-zero voxels of the plurality of pixels along the at least one fiber tract.

5. An imaging system-, comprising:
a magnetic resonance image unit;
an apparatus according to claim 1;
wherein, the magnetic resonance imaging unit is configured to acquire the set of dMRI images, and provide the set of dMRI images to the apparatus,
and wherein, the apparatus is configured to output a neurological disease classification for the patient on the basis of the set of dMRI images.

6. A method of analyzing diffusion magnetic resonance imaging data, the method comprising:
a) providing a processing unit with a set of diffusion-weighted diffusion magnetic resonance imaging (dMRI) images of a patient's brain wherein three or more regions of the brain volume in the dMRI image set are segmented;
b) determining by the processing unit an estimate of an orientation of neurons at each voxel of a brain volume in the dMRI image set by
determining a spherical probability distribution function at each voxel of the brain volume relating to probabilities of diffusion in a given direction at each voxel based on the set of diffusion weighted images, and
determining an estimated orientation of neurons at each voxel by utilizing a peak in the spherical probability distribution function at each voxel;
determining by the processing unit at least one diffusivity feature for each voxel of the brain volume based on the set of diffusion-weighted images;
c) determining by the processing unit a plurality of fiber tracts in the brain volume in the dMRI image set, the determining comprising utilizing the estimated orientation of neurons at each voxel of the brain volume;
d) identifying by the processing unit a plurality of pairs of the segmented regions which are connected by fiber tracts to one another, and for each pair of connected segmented regions:
selecting by the processing unit a plurality of voxels along fiber-tracks connecting the pair or regions and;
providing the at least one diffusivity feature of each of the selected voxels as inputs to a multi-input deep neural network which comprises a respective sparse 3D convolutional neural network for each pair of segmented regions, wherein each respective sparse neural network outputs a respective feature vector for the pair of regions based on the input features;
e) determining by the processing unit a neurological disease classification, wherein the multi-input deep neural network concatenates the feature vectors generated for each of the pairs of brain regions in a further fully connected layer, and wherein an output of the multi-input deep neural network is the classification of the neurological disease; and
f) outputting by an output unit the neurological disease classification.

7. The method of claim 6, further comprising: determining, by the processing unit, at least one connectivity weight for each connected pair of segmented regions based on the number of fiber tracts that connect the two connected segmented regions.

8. The method of claim 6, further comprising: determining, by the processing unit, at least one connectivity weight for each pair of connected segmented regions based on at least one diffusivity feature associated with each of a plurality of voxels along fiber tracts that connect the two connected segmented regions.

9. The method of claim 6, further comprising: selecting, by the processing unit, voxels to be input to the multi-input deep neural network for active or non-zero voxels of the plurality of pixels along the at least one fiber tract.

10. A computer programing comprising machine executable instructions stored on a non-transitory computer readable medium for execution by a processing unit, wherein when executed causes the processing unit to perform the method of claim 6.

* * * * *